United States Patent [19]

Ritzi

[11] 4,266,871

[45] May 12, 1981

[54] APPARATUS FOR VISUALLY DUPLICATING GEMSTONES

[75] Inventor: Thomas F. Ritzi, Daytona Beach, Fla.

[73] Assignee: Gem Instruments Corporation, Santa Monica, Calif.

[21] Appl. No.: 928,771

[22] Filed: Jul. 28, 1978

[51] Int. Cl.$^3$ .......................................... G01N 21/00
[52] U.S. Cl. ...................................... 356/30; 356/420
[58] Field of Search ................. 356/30, 402, 403, 416, 356/419–425

[56] References Cited

U.S. PATENT DOCUMENTS

| | | | |
|---|---|---|---|
| 961,852 | 6/1910 | Fujita | 356/403 |
| 2,867,916 | 1/1959 | Birdseye | 356/420 X |

*Primary Examiner*—F. L. Evans
*Attorney, Agent, or Firm*—Lyon & Lyon

[57] ABSTRACT

An apparatus visually duplicates the hue, tone, intensity and shape of a selected gemstone by combining predetermined intensities of red, green and blue light sources within a color mixing box. A single variable intensity light source and a monochromatic filter provide each of the three colors. Colored light from each light source is passed through a portion of a multi-segment diffusion lens prior to entering the color mixing box. The three separate colors are combined within the color mixing box and reflected from an image wheel which includes various geometric patterns. Light propagated from the color mixing box passes through a silhouette wheel to a crystal wheel which provides an appropriate gemstone shape. The light then passes through an image magnifier which controls the apparent size of the gemstone. Controls are provided to modify the shape, color and intensity of the duplicated gem displayed by the apparatus.

33 Claims, 11 Drawing Figures

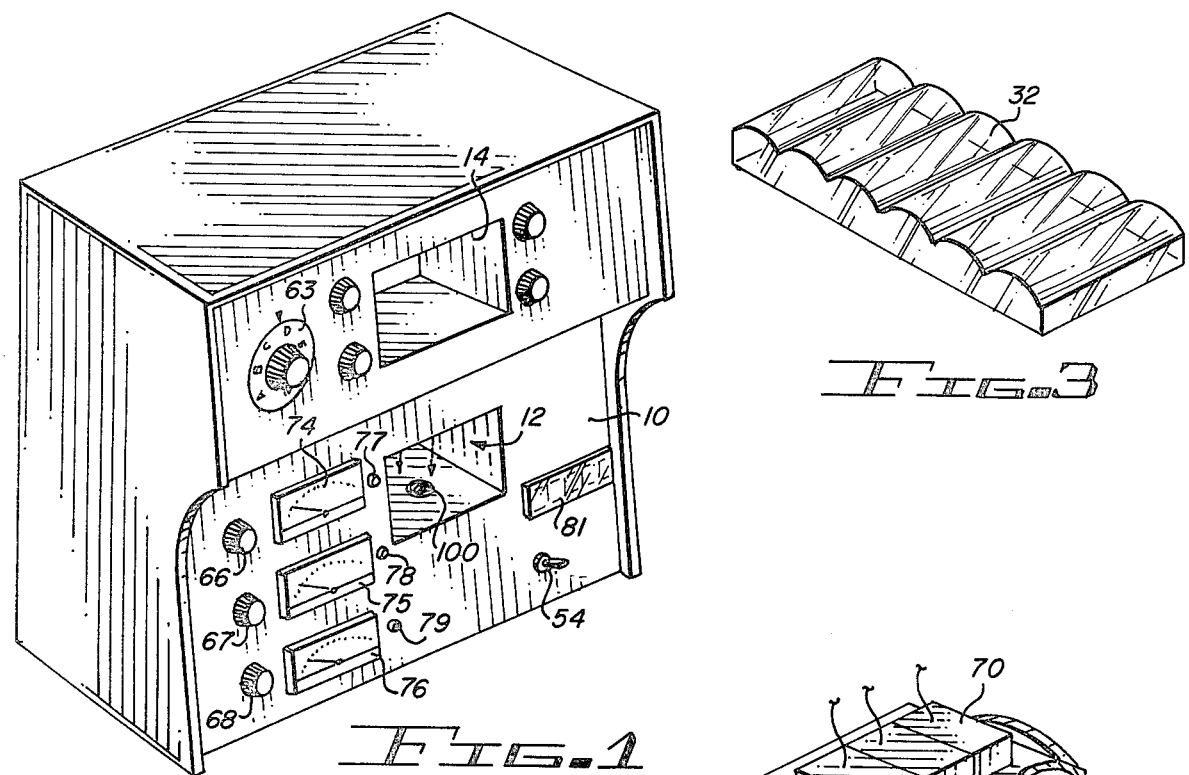
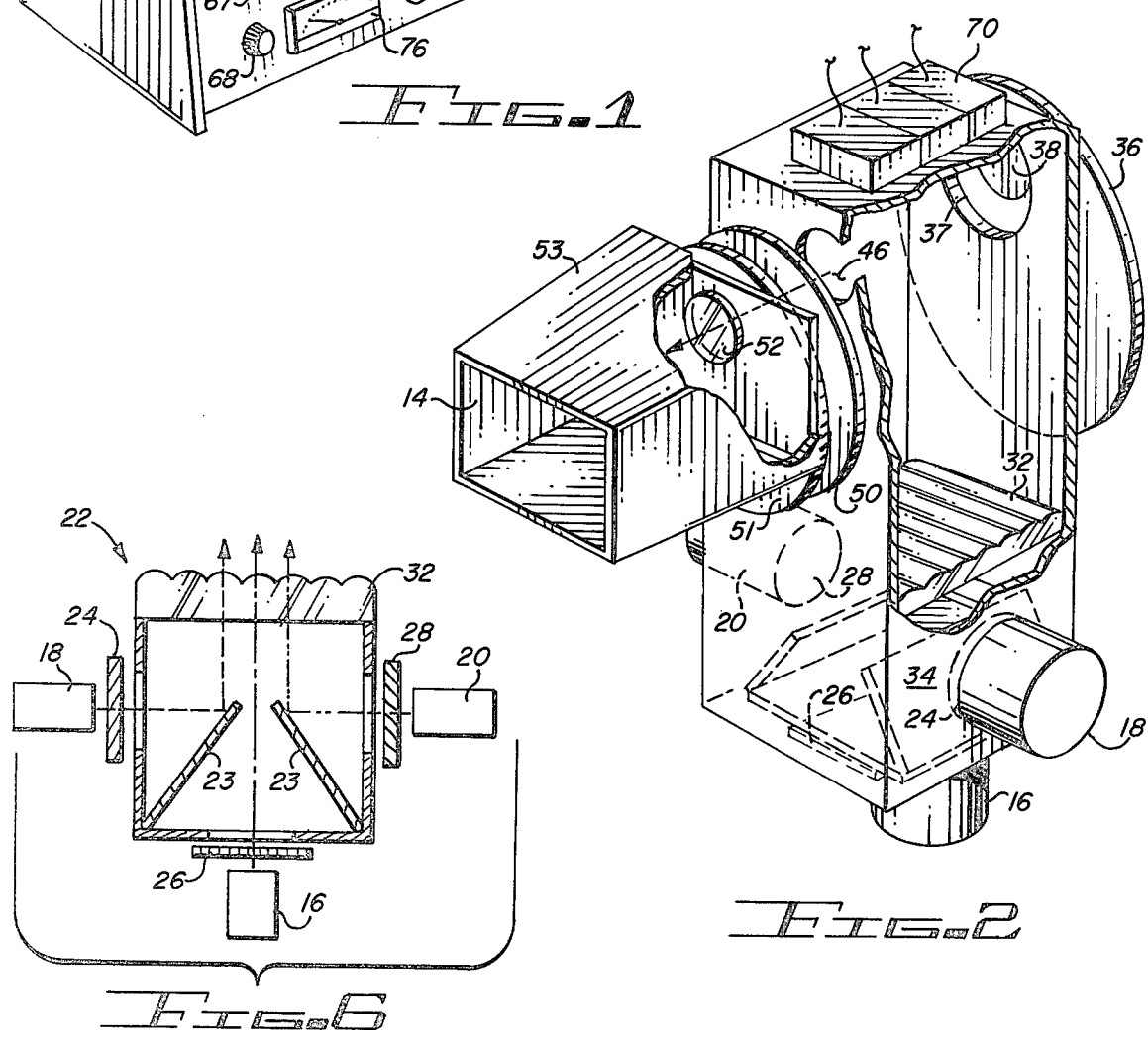

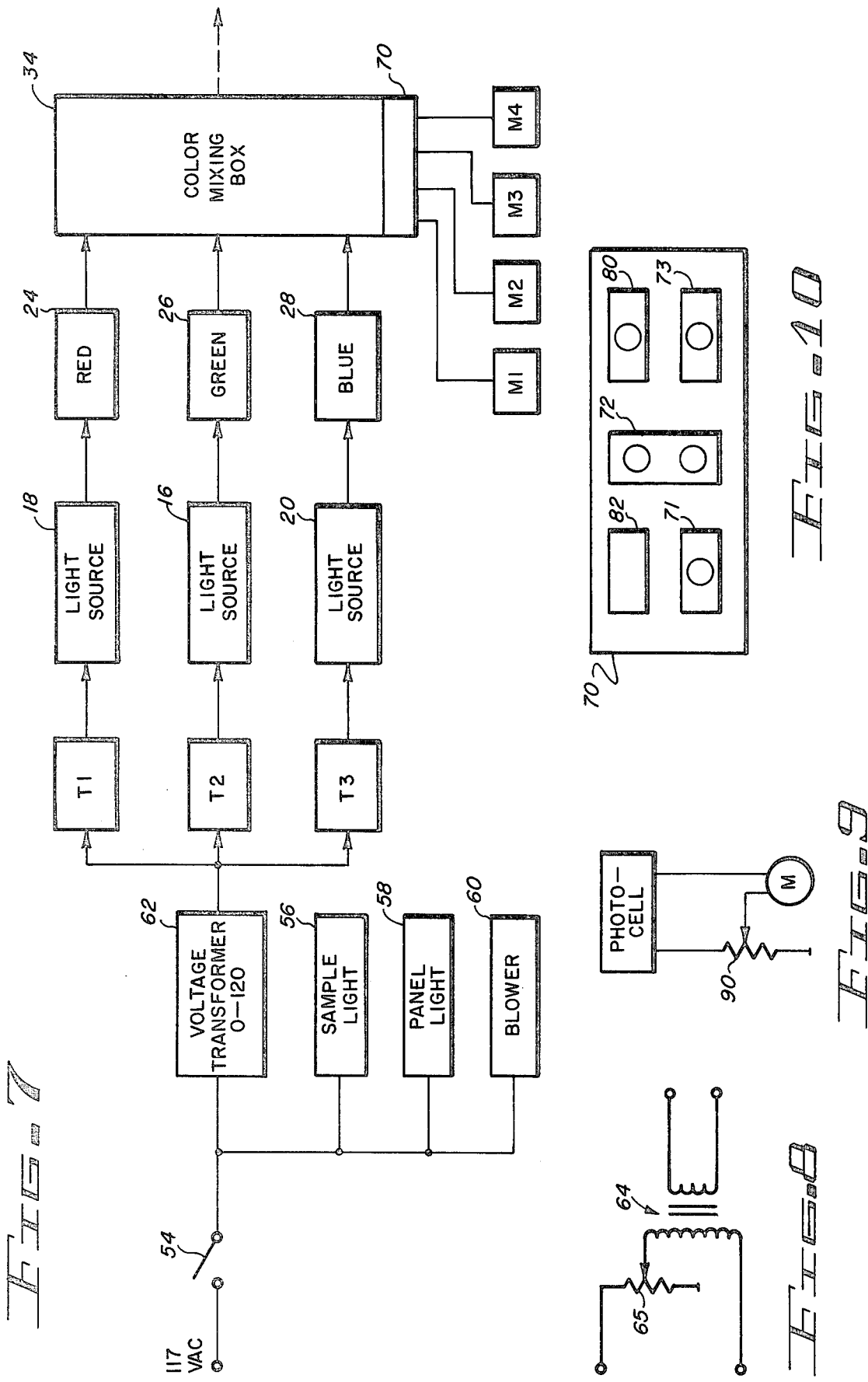

APPARATUS FOR VISUALLY DUPLICATING GEMSTONES

BACKGROUND OF THE INVENTION

1. Field of the Invention

The present invention relates to optical comparison devices and more particularly to a device for generating an image of a gemstone.

2. Description of the Prior Art

The prior art includes a number of inventions for analyzing various physical characteristics of gemstones. U.S. Pat. No. 4,012,141 (Hanneman) discloses an apparatus for identifying gemstones by measuring the relative reflectance of the stone being analyzed. U.S. Pat. No. 2,960,909 (Shipley) discloses an apparatus having rotating color filters for passing a concentrated beam of light through a gemstone. A light sensitive cell in this invention measures the intensity of the light passing through the gem. Color filters are provided to measure the light transmissivity of the gemstone for various different colors of light.

U.S. Pat. No. 3,467,475 (Celio) discloses a densitometer incorporating individually controllable color filters for comparing an unknown gemstone to a standard. U.S. Pat. No. 3,539,264 (Moore) discloses an optical comparator for gemstones having a lamp and an optical system for projecting lights through a gemstone and for projecting a silhouette of the gemstone on a screen.

Other relevant prior art is disclosed in the following U.S. Pat. Nos. 3,989,379 (Eickhorst); 3,867,032 (Bruck); 3,529,895 (Pincus); 1,744,485 (Michel); 3,858,979 (Elbe); 3,944,368 (Beesley); 2,421,344 (Mass); 3,520,660 (Webb); 3,237,509 (Fielding) and 3,762,817 (Harklau).

SUMMARY OF THE INVENTION

The present invention contemplates an apparatus for visually duplicating gemstones comprising a housing having a viewing port. Color mixing means is positioned within the housing and communicates with the viewing port. Red, green and blue light sources are optically coupled with the color mixing means. Means is also provided for selectively changing the intensity of the output of the red, green and blue light sources within the color mixing means to thereby change the color and intensity of light exiting the apparatus through the viewing port in order to either generate or duplicate a selected gemstone.

DESCRIPTION OF THE DRAWINGS

The invention is pointed out with particularity in the appended claims. However, other objects and advantages together with the operation of the invention, may be better understood by reference to the following detailed description taken in connection with the following illustrations wherein:

FIG. 1 is an illustration of the front panel of the housing for the present invention.

FIG. 2 is a cross sectional diagram of the internal mechanical structure of the invention.

FIG. 3 is a perspective view of the multi-segment diffusing lens utilized in the present invention.

FIG. 6 is a cross sectional view of the premix box of the present invention.

FIG. 7 is a block diagram of the electrical elements of the present invention.

FIG. 8 is an electrical schematic diagram of a variable voltage light source power supply utilized in the present invention.

FIG. 9 is a schematic diagram of the meter system used to detect each color intensity level.

FIG. 10 illustrates the lower surface of the housing for the photocells.

DESCRIPTION OF THE PREFERRED EMBODIMENT

Figure 4:
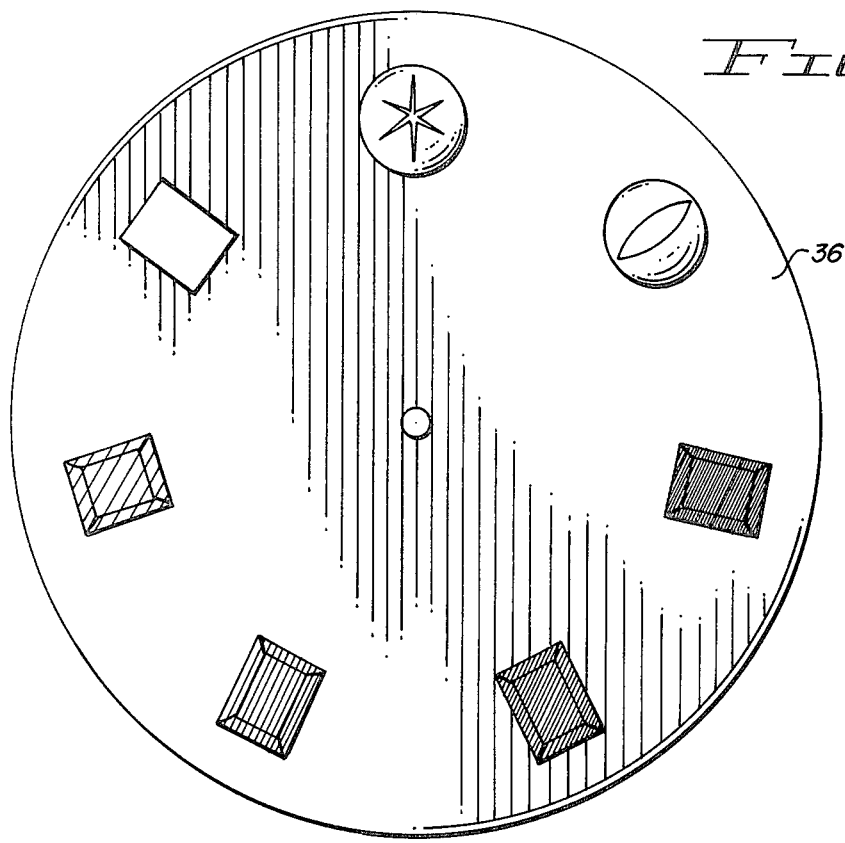
FIG. 4 is a front view of the image wheel of the present invention showing the patterns thereon.

In order to better illustrate the advantage of the invention and its contributions to the art, a preferred hardware embodiment of the invention will now be described in some detail.

Referring to FIGS. 1 and 2, the present invention is positioned within a housing 10 having an illuminated gemstone receptacle 12 and a viewing port 14 for viewing a gemstone duplicated by the present invention.

Referring also to FIG. 6, three identical 150 watt quartz halogen light sources 16, 18 and 20 are positioned on the lower side and on each opposing side of a premix box 22. Premix box 22 is a commercially available product which includes an aperture for receiving a beam of light from each light source and a pair of baffles 23 for reflecting and diffusing the light from the various light sources within the premix box. All of the interior surfaces of premix box 22 have a highly polished, mirror-like finish. Monochromatic filters 24, 26 and 28 are positioned between light sources 16, 18 and 20 and the outer surface of premix box 22. Filter 24 transmits red light, while filters 26 and 28 transmit respectively green and blue light.

The light emitted from filters 24, 26 and 28 passes into the interior of premix box 22 and is mixed and redirected upward through a multi-segment diffusion lens 32 and then into the interior of color mixing means or color mixing box 34.

FIG. 3 more clearly illustrates the configuration of lens 32. The various segments of lens 32 refract and diffuse the three colors of monochromatic light uniformly over the interior of mixing box 34. The interior of mixing box 32 is painted black so that the interior surface of the box will not alter the color content of the light within the box.

Referring now to FIGS. 2 and 4, an image wheel 36 is positioned immediately behind an aperture 37 in the rear portion of mixing box 36. The front surface of image wheel 36 is generally solid black in color, but includes seven specific patterns. One of these patterns is configured as shown in FIG. 4 to resemble the general appearance of a star sapphire, while another image is generally white in color. A plurality of rectangular images are provided which resemble the general configuration of the back facets of a faceted gemstone. Each of these plurality of back facet configurations contains a varying degree of black coloration to assist in reproducing the back facet configuration of various types of gemstones. In the preferred embodiment of the invention, each image is derived by making a black and white photograph of the rear side or back facets of an actual gemstone. This photograph is used to make a black and white print several times larger than the stone photographed. The largest dimension of each rectangular image is about 2½". The image wheel visually reproduces the internal structure of selected gemstones as is typically seen through the upper surface of a mounted or unmounted gemstone.

The front of color mixing box 34 includes an aperture 46 to emit the light which has been reflected from the interior surfaces of color mixing box 34 and from the selected pattern 38 of image wheel 36. The hue, tone, intensity and appearance of the light emitted from port 46 is controlled and modified by the intensity of the light emitted by light sources 16, 18 and 20 and by the pattern 38 which is positioned behind aperture 37 of mixing box 34.

Figure 5A:
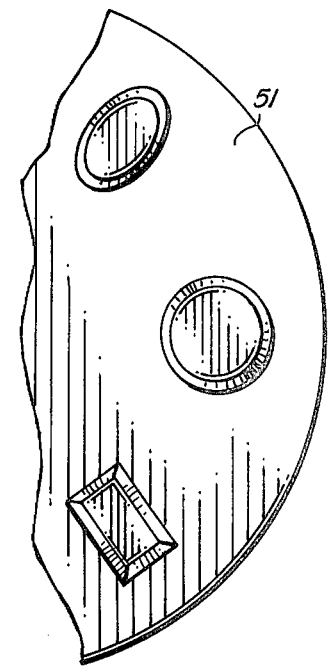
FIG. 5A illustrates the crystal wheel of the present invention.
Figure 5:
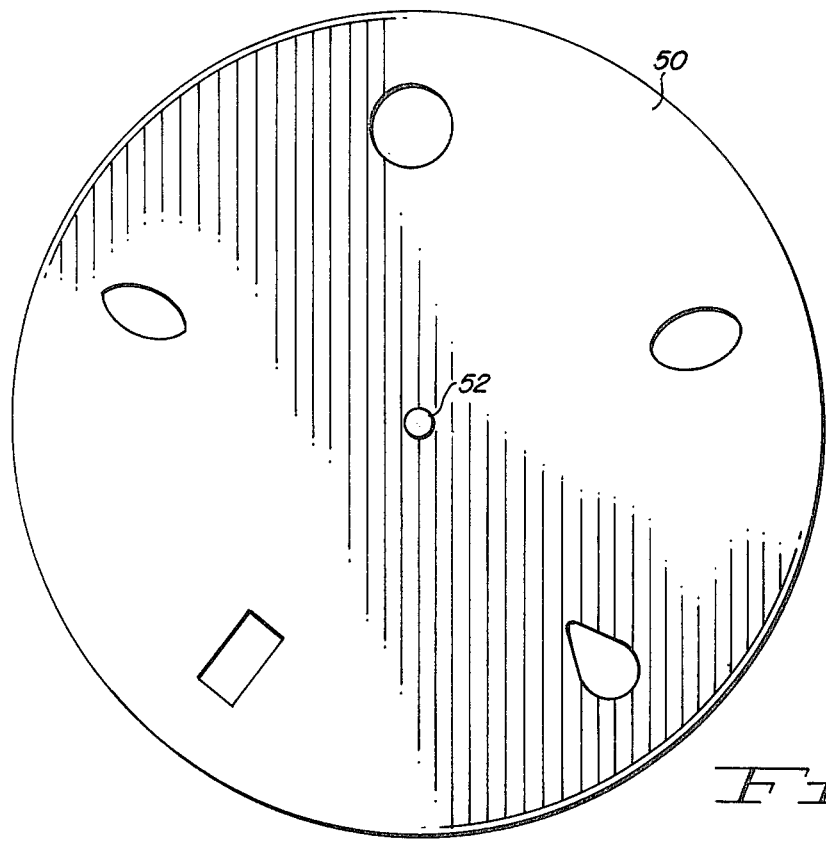
FIG. 5 illustrates the silhouette wheel of the present invention.

Referring to FIGS. 2, 5, and 5A, a silhouette wheel 50 and a crystal wheel 51 include a plurality of apertures which can be rotatably aligned with the light emitted from port 46 of mixing chamber 34. Silhouette wheel 50 contains a plurality of apertures having marquis, pear and other various configurations which are designed to simulate the shape of commonly available gemstones. Crystal wheel 51 includes rectangular, oval and round transparent crystals having flat bottom surfaces and a faceted upper surface as shown in FIG. 5A. A magnifying watch crystal may be used as the round crystal. Transparent spinel can also be used in crystal wheel 51 since it is a gemstone of relatively low cost.

A concave plano lens 52 is positioned in alignment with the light path from port 46 and is movable in a fore and aft direction in order to control the size of the image which appears in viewing port 14. FIG. 1 illustrates that a plurality of four knobs is positioned about viewing port 14. One of these knobs is used to control the fore and aft position of lens 52, while the three remaining knobs are used to control the rotary position of the image wheel 36, silhouette wheel 50 and crystal wheel 51 to provide the appropriate size and appearance of the gemstone projected through viewing port 14. A light shield 53 extends between crystal wheel 51 and the rear surface of the front panel of housing 10 in order to prevent stray light from interfering with the image projected through viewing port 14.

Referring now to FIG. 7, a block diagram of the electrical structure of the invention is illustrated. An on/off switch 54 selectively connects and disconnects a source of 117 volt AC power to the present invention. When switch 54 is in the closed position, sample lights 56 and 58 and cooling blower 60 are energized. Sample lights 56 and 58 are in the same receptical and used to illuminate a gemstone which is positioned in gemstone receptacle 12 and comprises an incandescent light and two florescent lights. The lighting provided by sample lights 56 and 58 should generally produce color temperatures of between 3200 to 6000 degrees Kelvin. Blower 60 is a small electric blower which is incorporated to remove the heat generated by the light sources positioned within the interior of housing 10. In the preferred embodiment, blower 60 has an air handling capacity of 115 cubic feet per minute.

Variable voltage transformer 62 is also energized by the closure of switch 54 and provides an alternating current output voltage varying in magnitude from zero to 117 volts. A dial 63 on the front panel of housing 10 is provided to control the output voltage from transformer 62. Dial 63 includes markings which permit the operator of the present invention to approximately set the output voltage of transformer 62.

Variable output voltage transformers T1, T2 and T3 are provided to independently provide the desired AC output voltage to light sources 16, 18 and 20. FIG. 8 illustrates the internal components of each of the units T1, T2 and T3. The input voltage to transformer 64 is controlled by potentiometer 65 which is coupled as shown. The output voltage from transformer 64 which is used to power one of the light sources is thus readily adjusted. Knobs 66, 67 and 68 control the position of the wiper arm of potentiometer 65 of T1, T2 and T3 in order to control the intensity of illumination provided from each of the light sources.

Referring now to FIGS. 1, 7 and 10, a photocell housing 70 is positioned adjacent to an aperture in the upper surface of mixing box 34. The lower surface of housing 70 includes a plurality of apertures as is shown in FIG. 10. Aperture 71 contains a green filter, while apertures 72 and 73 include respectively blue and red filters. Each of the filters 71, 72 and 73 must be exactly equivalent to filters 24, 26 and 28.

A silicon photocell is positioned behind the filters for convering apertures 71 and 73. A pair of silicon photocells is positioned behind the blue filter covering aperture 72. The electrical output from the photocells behind each aperture and housing 70 are coupled individually to meters 74, 75 and 76 on the front panel of housing 10. FIG. 9 indicates that an adjustable potentiometer 77 is coupled between the silicon photocell and each meter in order to calibrate the meter. Two photocells are required to sense the intensity of the blue light in color mixing box 34 since the electrical output from a single photocell is insufficient to properly drive the meter which senses the intensity of blue light. Access holes 77, 78 and 79 are positioned in the vincinty of the meters on the front panel of housing 10 to permit access to the adjustable potentiometer 77 associated with each meter circuit.

An additional part 80 is provided in the lower surface of photocell housing 70. Another silicon photocell is positioned by aperture 80 and is coupled to a digital volt meter which includes a digital meter display 81 on the front panel of housing 10. This digital volt meter is of the type commercially available of which is an extremely high accuracy. An additional port 82 is provided in the lower portion of photocell housing 70. Port 82 is only used in connection with a master calibration unit at the factory to properly calibrate the photocell by aperture 80 with the digital volt meter. Since the digital volt meter within each unit is of extremely high accuracy and drifts little over a lengthy period of time, the calibration of the digital volt meter/silicon photocell combination is rarely required.

Periodic recalibration of meters 74, 75 and 76 and their associated photocells within housing 70 is readily accomplished. The illumination intensity control 66, 67 and 68 for light sources 18, 16 and 20 are adjusted so that these light sources are de-energized. Knob 66 which energizes light source 18 to produce red light within color mixing box 34 is rotated clockwise until a predetermined reading is obtained on the digital meter read out 81. At this predetermined read out value, meter 74 should read a corresponding predetermined value. If this corresponding predetermined value is not obtained, meter potentiometers 80 is adjusted so that meter 74 reads the appropriate value when the digital meter read out indicates the value set by knob 66. Once this calibration has been completed, knob 66 is rotated to de-energize light source 18. A similar procedure is followed to calibrate meters 75 and 76. In each case, only a single light source energized during the calibration process.

One of the primary uses of the present invention is to permit two jewellers each having an apparatus of the present invention and geographically separated from one another to accurately communicate a complete color and configuration description of a selected gemstone by merely placing a telephone call and exchanging data corresponding to meter readings and to the settings for the image, silhouette and crystal wheels. The approximate setting of transformer 62 is obtained by designating the range of rotation of knob 63. Since the digital volt meter of each unit has been calibrated at a central location, and after calibrating each instrument in the field, an exchange of the data set forth above between two geographically separated units assures that each unit will project an identical image.

Typically jeweller 1 located in city A will have a gemstone 100 which he would like to sell to jeweller 2 in city B. In order to determine the appropriate parameters to communicate to jeweller 2, jeweller 1 places the stone 100 in tray 12 of the present invention and activates switch 54. Jeweller 1 selects the silhouette and crystal which corresponds to the shape of gemstone 100 by rotating the knob on the front panel of housing 10 to select the appropriate apertures of the silhouette and crystal wheels. Jeweller 1 then adjusts dials 63 and knobs 66, 67 and 68 to vary the intensity of the red, green and blue light sources so that the color of the gemstone appearing in viewing port 14 exactly and precisely duplicates the color of gemstone 100. Jeweller 1 also adjusts the lens positioning knob to displace lens 52 so that the size of the image in viewing port 14 corresponds exactly with the geometric size of gemstone 100. Jeweller 1 also adjusts the knob which rotates image wheel base 36 so that the pattern which most closely simulates the appearance of gemstone 100 is positioned directly behind aperture 37 of color mixing box 34. Once jeweller 1 has completed this procedure, he writes down the meter intensity readings from meters 74, 75 and 76 and the position indexes of the knobs which control the operation of image wheel 36, silhouette wheel 50, crystal wheel 51 and lens 52. These parameters are communicated by telephone to jeweller 2 who calibrates his instrument and adjusts it so that the meter readings and knob settings on his machine duplicate those on the machine of jeweller 1.

Jeweller 2 is thus able to duplicate an image of gemstone 100 on his own instrument which accurately and precisely duplicates the hue, tone, intensity, faceting and shape of gemstone 100 which is located miles away in city A.

Using variations of the method described above, a jeweller who needs to exactly match a stone which he is working with, can readily communicate to other tradesmen to exact requirements so that they can inform him whether they have the appropriate stone or cannot supply his needs. Using other variations of this same method, the present invention can be used as an educational tool to expose gemologist trainees to a variety of gemstones far more extensive than they might ever come in contact with during years of work experience.

The present invention can also be used to assist a jeweller in establishing a permanent appraisal record for a stone which in the future might not be physically available. Customers are also able to utilize the present invention to ascertain the exact size, shape, faceting and color of the stone which they would like to order. The ordering of a selected stone from a large gemstone supplier can then be accomplished merely by communicating the adjustment parameters of the present invention. In this way, wordy, ambiguous terms are no longer required to exactly and accurately describe various characteristics of a gemstone.

It will be apparent to those skilled in the art that the disclosed apparatus for visually reproducing gemstones may be modified in numerous ways and may assume many embodiments other than the preferred forms specifically set out and described above. Accordingly, it is intended by the appended claims to cover all such modifications of the invention which fall within the true spirit and scope of the invention.

I claim:

1. Apparatus for reproducing the color and intensity of a selected gemstone, comprising:
    a housing having a viewing port;
    a source of light of variable frequency within said housing;
    means for selectively changing the frequency of said light to obtain variations in the color of said light passing through said port;
    means for changing the intensity of said light passing through said port, whereby changes in the intensity of colored light exiting said viewing port may be controlled to conform with said selected gemstone; and
    imaging means optically coupled between said light source means and said viewing port for visually duplicating the structural appearance of the selected gemstone.

2. The apparatus recited in claim 1, said imaging means further comprising a restrictive orifice between said light source and said port said orifice having a shape corresponding to the shape of said selected gemstone.

3. The apparatus recited in claim 2, said imaging means further comprising means for changing the size of the image of said orifice passing through said port.

4. The apparatus recited in claim 1, said imaging means further comprising a transparent crystaline member between said light source and said port.

5. The apparatus recited in claim 4 wherein said imaging means includes means for varying the size of the image.

6. The apparatus recited in claim 1 further comprising means adjacent said part for supporting said selected gemstone.

7. The apparatus recited in claim 6 further comprising two variable Kelvin temperature white lights mounted on said housing for illuminating said selected gemstone.

8. The apparatus of claim 3 wherein said size changing means includes a lens displaceable with respect to said viewing port.

9. Apparatus for visually reproducing a selected gemstone, comprising:
    a housing having a viewing port;
    color mixing means within said housing and communicating with said port;
    means for generating red, green and blue light beams optically coupled with said color mixing means;
    means coupled to said light generating means for selectively changing the intensity of the red, green and blue light beams to produce a light output from said color mixing means which visually duplicates the hue, tone and intensity of the selected gemstone; and imaging means optically coupled between said generating means and said viewing port for visually duplicating the structural appearance of the selected gemstone.

10. The apparatus of claim 9 wherein said color mixing means includes a first aperture communicating with said viewing port and a second aperture aligned with said viewing port and said first aperture, and said imaging means includes an image wheel rotatably coupled to said mixing box and having a plurality of images positioned about the periphery of said wheel, wherein selected ones of said images are positionable in alignment with said second aperture to permit light within said mixing means to be reflected from selected images through said first and second apertures to said viewing port.

11. The apparatus of claim 10 wherein said structure duplicating means includes a transparent crystaline structure having parallel oriented upper and lower surfaces, said structure being positioned in alignment with the beam of light travelling from said first aperture and to said viewing port and having said upper and lower surfaces oriented perpendicular to the beam of light.

12. The apparatus of claim 11 further including a plurality of transparent crystaline structures each having a distinct geometric shape and means for positioning a selected one of said transparent crystaline structures in the beam of light traveling between said first aperture and said viewing port.

13. The apparatus of claim 12 wherein said positioning means for said plurality of transparent crystaline structures includes a crystal wheel having said plurality of transparent crystaline structures positioned around the periphery thereof.

14. The apparatus of claim 9 wherein said color mixing means includes a first aperture communicating with the viewing port and the imaging means further includes means positioned between said first aperture and said viewing port for passing light in a beam having a predetermined silhouette.

15. The apparatus of claim 14 wherein said silhouette means further includes a body having an aperture the outline of which is configured in the form of a selected silhouette.

16. The apparatus of claim 9 further including means positioned between said generating means and said color mixing means for diffusing the red, green and blue light beams.

17. The apparatus of claim 16 wherein said diffusing means includes a multi-segment lens.

18. The apparatus of claim 9 wherein said duplicating means includes a two dimensional reproduction of the three dimensional structural appearance of a selected gemstone.

19. The apparatus of claim 18 wherein said two dimensional reproduction includes a black and white photograph of the structural appearance of a selected gemstone.

20. Apparatus for reproducing an image of a selected gemstone comprising
a housing having a viewing port,
variable light source means in optical communication with said viewing port for producing selectable intensities of a plurality of wavelengths of light, and
imaging means optically coupled between said light source means and said viewing port for providing a visual image of the selected gemstone.

21. The apparatus of claim 20 wherein said variable light source means includes color mixing means.

22. The apparatus of claim 20 wherein said imaging means includes means for simulating the internal structure of the selected gemstone.

23. The apparatus of either claims 20, 21 or 22 wherein said imaging means includes aperture means for simulating the shape of the selected gemstone.

24. The apparatus of claim 23 wherein said imaging means includes transparent member means for further simulating the shape of the selected gemstone.

25. The apparatus of claim 20, 21 or 22 wherein said imaging means includes image sizing means for varying the size of the image of the selected gemstone.

26. The invention of claim 22 wherein said means for simulating the internal structure of the selected gemstone comprises a member having a plurality of images therein corresponding to the internal structure of a plurality of gemstones, each image being individually selectable.

27. The invention of claim 23 wherein said means for simulating the shape of the selected gemstone comprises a member having a plurality of apertures therein corresponding to the shape of a plurality of gemstones, each aperture being individually selectable.

28. The invention of claim 24 wherein said transparent member means includes a plurality of transparent members corresponding to at least a portion of the faceted shape of a plurality of gemstones, each transparent member being individually selectable.

29. The invention of claim 20 further comprising
means for detecting the intensity of said of said pluralities of wavelengths of light, and
a plurality of indicating means responsive to said detecting means for indicating the intensity of each of said pluralities of wavelengths of light.

30. The invention of claim 29 further including
means for varying the intensity of said plurality of wavelengths of light individually and collectively.

31. The invention of claim 20 further comprising
means for supporting the selected gemstone; and
means for illuminating the selected gemstone in said support means.

32. The invention of claim 29 wherein said detecting means comprises a plurality of photodetectors and said indicating means comprise foot candle balance meters.

33. The invention of claim 20 wherein said plurality of wavelengths of light produced by said variable light source means comprises at least red, blue and green.

* * * * *